US012761175B2

(12) United States Patent
Kosinski

(10) Patent No.: US 12,761,175 B2
(45) Date of Patent: Oct. 13, 2026

(54) METHOD AND APPARATUS FOR REMOTE MONITORING OF VARIOUS ORGANIC COMPOUNDS

(71) Applicant: VIOVOC LLC, Scottsdale, AZ (US)

(72) Inventor: Lawrence R. Kosinski, Scottsdale, AZ (US)

(73) Assignee: VIOVOC LLC, Scottsdale, AZ (US)

( * ) Notice: Subject to any disclaimer, the term of this patent is extended or adjusted under 35 U.S.C. 154(b) by 481 days.

(21) Appl. No.: 18/356,491

(22) Filed: Jul. 21, 2023

(65) Prior Publication Data

US 2024/0027383 A1 Jan. 25, 2024

Related U.S. Application Data

(60) Provisional application No. 63/391,424, filed on Jul. 22, 2022.

(51) Int. Cl.
*G01N 27/12* (2006.01)
*G01N 33/00* (2006.01)

(52) U.S. Cl.
CPC ....... *G01N 27/125* (2013.01); *G01N 33/0047* (2013.01)

(58) Field of Classification Search
CPC ............. G01N 27/125; G01N 33/0047; G01N 2001/2276; G01N 27/12; G01N 2001/245; G01N 33/0009
See application file for complete search history.

(56) References Cited

U.S. PATENT DOCUMENTS

2016/0350514 A1* 12/2016 Rajendran .............. G06Q 10/10
2017/0074857 A1 3/2017 Dennis et al.
(Continued)

FOREIGN PATENT DOCUMENTS

EP 1099102 A1 5/2001
EP 3660498 A1 6/2020
WO 2019135232 A1 7/2019

OTHER PUBLICATIONS

Neyrinck et al, "Noninvasive monitoring of fibre fermentation in healthy volunteers by analyzing breath volatile metabolites: lessons from the FiberTAG intervention study" Gut Microbes, 2021, 13(1) pp. 1-16. (Year: 2021).*
(Continued)

*Primary Examiner* — Dennis White
(74) *Attorney, Agent, or Firm* — Bookoff McAndrews, PLLC

(57) ABSTRACT

A monitoring device for measuring organic compounds may include a housing of the monitoring device. The housing may be defined by an outer peripheral wall. The outer peripheral wall may include at least a first surface and a second surface opposite the first surface. The monitoring device may further include an interior cavity disposed within the housing. The monitoring device may further include a fan disposed within the interior cavity. The monitoring device may further include a plurality of slots in the first surface. The plurality of slots may be disposed directly above the fan and may be configured to allow the fan to pull ambient air from an environment outside of the housing into the interior cavity. The monitoring device may further include a visual indicator disposed on the first surface. The monitoring device may further include one or more buttons disposed on the first surface.

20 Claims, 12 Drawing Sheets

(56) References Cited

U.S. PATENT DOCUMENTS

| | | | |
|---|---|---|---|
| 2020/0077923 A1 | 3/2020 | Wang et al. | |
| 2020/0182843 A1* | 6/2020 | Park | H05K 1/18 |
| 2020/0386731 A1 | 12/2020 | Weiss-Penzias et al. | |
| 2022/0007972 A1* | 1/2022 | Thors | A61B 5/097 |

OTHER PUBLICATIONS

International Search Report issued in International Application No. PCT/US2023/070684 dated Oct. 25, 2023 (10 pages).

Advanced Bread and Pastry—A Professional Approach: Michael Suas, Delmar Cengage Learning 2009.

Clemmensen C, Muller TD, Woods SC, Berthoud HR, Seeley RJ, Tschop MH. Gut brain cross-talk in metabolic control. Cell. 2017; 168(5):758-74.

Clinical Gastroenterology and Hepatology 2020;18:1054-1069.

Clinical Gastroenterology and Hepatology 2021;19:1189-1199.

Dejea, C. et al. Microbiota organization is a distinct feature of proximal colorectal cancers. Proc. Natl Acad.Sci USA 111, 18321-18326 (2014).

Desai, M S. et al. A dietary fiber-deprived gut microbiota degrades the colonic mucus barrier and enhances pathogen susceptibility. Cell 167. 1339-1353 (2016).

Donohoe, D. R., Collins, L. B., Wali A.,Bigler, R., Sun, W. and Bultman, S. J., Mol. Cell, 2012, 48(4), 612-626.

Gastroenterology 2022;162:1574-1582.

Gastroenterology vol. 162, No. 7; P1858-1875.

Gastroenterology vol. 160, No. 6: 2029.

Gastroenterology: vol. 162, #7: P1911-1932, Jun. 1, 2022.

GBD 2017 Colorectal Cancer Collaborators. The global, regional, and national burden of colorectal cancer and its attributable risk factor in 195 countries and territories 1990-2017: a systematic analysis for the Global Burden of Disease Study 2017. Lancet Gastroenterol. Hepatol. 4. 913-933 (2019).

Janney, A., Powrie, F. & Mann, E.; Nature vol. 585, P509, (2020).

Keum, N. & Giovannucci, E. Global Burden of Colorectal Cancer: emerging trends, risk factors and prevention strategies. Nat. Rev. Gastroenterol. Hepatol. 16. 713-732 (2019).

Kleiner DE, Brunt EM, Wilson LA, et al. Association of histologic disease activity with progression of nonalcoholic fatty liver disease. JAMA Netw Open 2019;2:e1912565.

Lee WJ, Hase K. Gut microbiota-generated metabolites in animal health and disease. Nat Chem Biol. 2014; 10 (6):416-24.

Megan W. Bourassa, Ishraq Alim, Scott J. Bultman, et al., "Butyrate Neuroepitenetics and the Gut Microbiome: Can a Higher Fiber Diet Improve Brain Health?" Neuroscience Letters 625 (Jun. 2016) 56-63. https://www.sciencedirect.com.

N Engl J Med 2003;349:1360-8.

N Engl J Med 2014; 371:944-951.

N Engl J Med 2017;376:2566-78.

N Engl J Med 2018;379:1635-42.

Oleesen, S. W. & Alm, E.J> Dysbiosis is not an answer. Nat. Microbiol. 1. 16228 (2016).

Smith, P. A., Nature, 2015, 526, 312-314.

Tartine Bread: Chad Robertson, Chronicle Books 2010.

Van de Wouw M, Schellekens H, Dinan TG, Cryan JF. Microbiotagut-brain axis: modulator of host metabolism and appetite. J Nutr 2017;147:727-45.

Velcich, A et al. Colorectal cancer in mice geneticallyh deficient in the Mucin Muc2. Science 295, 1726-1729 (2002).

* cited by examiner

METHOD AND APPARATUS FOR REMOTE MONITORING OF VARIOUS ORGANIC COMPOUNDS

RELATED APPLICATIONS

This application is a nonprovisional of and claims the benefit of priority to U.S. Provisional Patent Application No. 63/391,424, filed Jul. 22, 2022, entitled METHOD AND APPARATUS FOR REMOTE MONITORING OF A PERSON'S DIETARY INTAKE, by Dr. Lawrence Kosinski, the entirety of which is hereby incorporated herein by reference.

TECHNICAL FIELD

The present disclosure generally relates to an apparatus and methods for remote monitoring of various organic compounds. More specifically, a person's dietary intake or various fermentation processes may be observed through the monitoring of various organic compounds.

BACKGROUND

The odor of a human stool results from the vaporization of volatile organic compounds (VOCs) contained in the stool into the atmosphere at the time of defecation. These VOCs are variable as the specific profile of VOCs in human stool depends on multiple factors including the content of the diet as well as the presence of certain disease processes. Disclosed herein, among other aspects, is a noninvasive tool for the monitoring of VOCs and other organic compounds in human stool.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY OF THE DISCLOSURE

According to certain aspects of the disclosure, an apparatus and methods are disclosed for monitoring organic compounds.

In one aspect, an exemplary embodiment of a monitoring device for measuring organic compounds may include a housing of the monitoring device. The housing may be defined by an outer peripheral wall. The outer peripheral wall may include at least a first surface and a second surface opposite the first surface. The monitoring device may further include an interior cavity disposed within the housing. The monitoring device may further include a fan disposed within the interior cavity. The monitoring device may further include a plurality of slots in the first surface. The plurality of slots may be disposed directly above the fan and may be configured to allow the fan to pull ambient air from an environment outside of the housing into the interior cavity. The monitoring device may further include a visual indicator disposed on the first surface. The monitoring device may further include one or more buttons disposed on the first surface.

In another aspect, an exemplary embodiment of a monitoring device for measuring organic compounds may include a housing of the monitoring device. The housing may be defined by an outer peripheral wall. The outer peripheral wall may include at least a first surface and a second surface opposite the first surface. The monitoring device may further include an interior cavity disposed within the housing. The monitoring device may further include a fan disposed within the interior cavity. The monitoring device may further include a plurality of slots in the first surface. The plurality of slots may be disposed directly above the fan and may be configured to allow the fan to pull ambient air from an environment outside of the housing into the interior cavity. The monitoring device may further include a sensor configured to receive the ambient air. The monitoring device may further include a visual indicator disposed on the first surface.

In a further aspect, an exemplary embodiment of a method of measuring organic compounds may include receiving, by a monitoring device, user data associated with a user of the monitoring device. The method may further include receiving, by the monitoring device, environmental data associated with the organic compounds of an environment. The method may further include measuring, by a sensor of the monitoring device, a change in a level of resistance of the sensor based on the environmental data. The method may further include comparing, by one or more processors, the change in the level of the resistance of the sensor to the user data. The method may further include transmitting, by a communications terminal of the monitoring device, the change in the level of the resistance of the sensor to a downstream entity.

It is to be understood that both the foregoing general description and the following detailed description are exemplary and explanatory only and are not restrictive of the disclosed embodiments, as claimed.

BRIEF DESCRIPTION OF DRAWINGS

Corresponding reference numerals indicate corresponding parts throughout the several views of the drawings.

DETAILED DESCRIPTION

Figure 1:
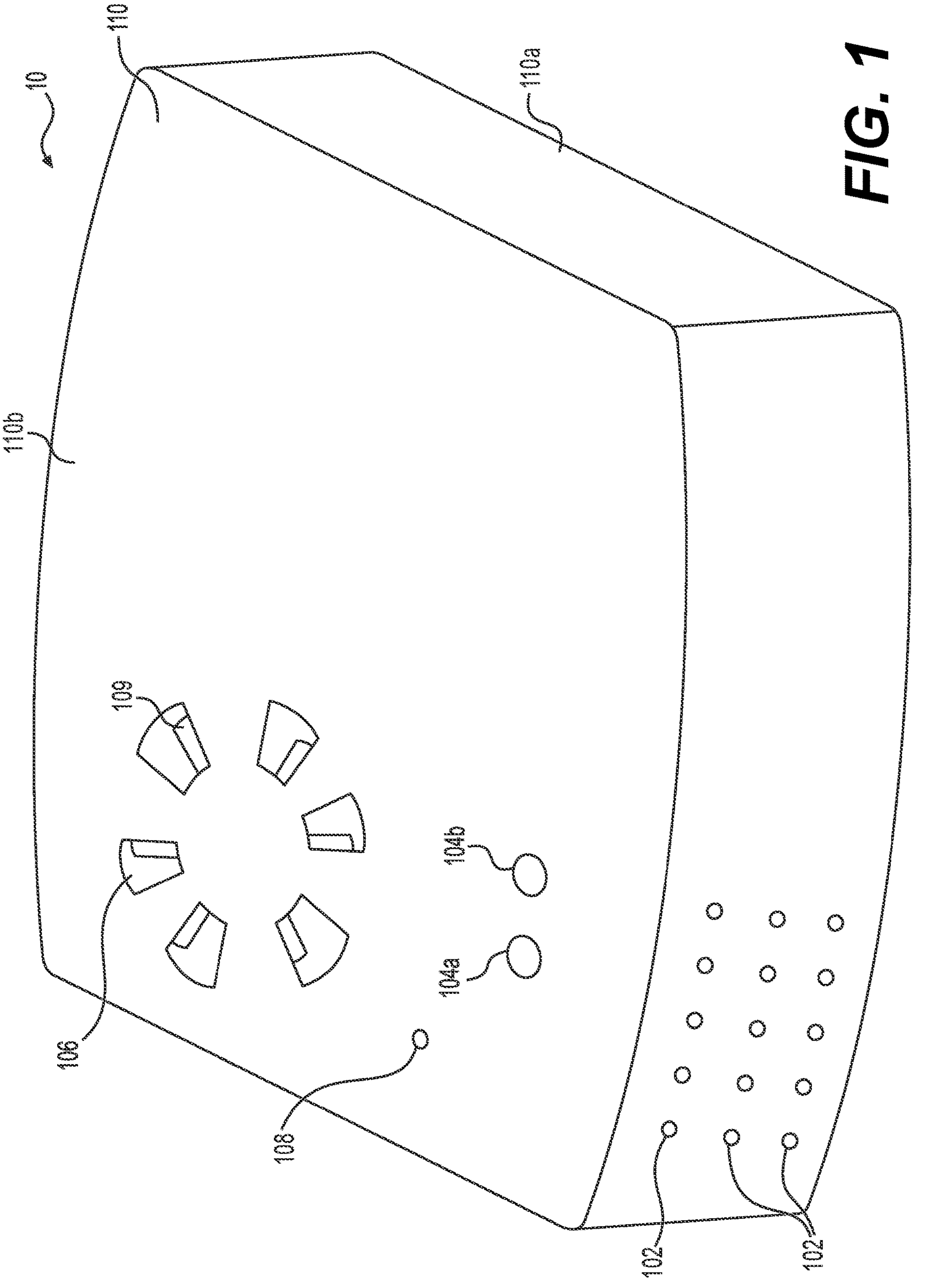
FIG. 1 illustrates a monitoring device, according to one or more embodiments.

An important challenge exists in monitoring a person's dietary intake and digestion that is important for both the medical monitoring and wellness needs of an individual. The true nutrient value of food goes beyond what is absorbed, as measured in grams of protein, carbohydrate, and fat. Further, fiber, and food that ingested but not absorbed, is equally important.

Although not absorbed, fiber becomes an essential part of food for the trillions of bacteria and other micro-organisms that inhabit the gastrointestinal (GI) tract, forming what is known as the fecal microbiome. These micro-organisms metabolize fiber into compounds that have profound effects on health affecting immune status, the risk of developing some cancers, the likelihood of developing diabetes, liver disease, obesity, dementia, among other aspects. Ultimately, the health of the fecal microbiome affects longevity of life.

Further, in order for diets to be effective, it is essential that patients remain compliant. Since most chronic health conditions are asymptomatic, the lack of immediate exacerbation of symptoms can allow disease progression without symptom development when compliance is lacking. Compliance with a diet must be particularly maintained in asymptomatic diseases to avoid unnecessary morbidity, which is difficult without regular and timely feedback to the patient.

Patient education is essential and effective, but nutrition is a complex issue, one that typically is only partially understood and becomes difficult to maintain by most people. There can be a challenge in both having a patient accurately monitor their dietary intake as well as knowing what adjustments they must make in their dietary intake to restore maintenance. This may become a chronic lifelong challenge.

Fortunately, the changes in the fecal microbiome associated with the ingestion of a high fiber diet result in the production of markers that can be measured. The bacteria in the fecal microbiome ferment fiber into short chain fatty acids (SCFAs) like butyrate, propionate, acetate, and other volatile organic compounds which are then vaporized into the air above a bowel movement. These VOCs can be measured in the air above the toilet, post-defecation, and may correlate with the amount of fiber in the diet.

Although gas chromatography and mass spectrometry can be used to measure the VOCs from these SCFAs, it represents a complex expensive process that is not conducive to mass distribution to the public. The present disclosure therefore represents a noninvasive device that can be distributed widely. The output can be received and maintained in cloud-based servers for analysis and feedback. Additionally, the present disclosure may detect products of fermentation as well as VOCs.

While the present disclosure may be described with respect to specific applications or industries, those skilled in the art will recognize the broader applicability of the disclosure.

The terms "a", "an", "the", "at least one", and "one or more" are used interchangeably to indicate that at least one of the items is present. A plurality of such items may be present unless the context clearly indicates otherwise. All numerical values of parameters (e.g., of quantities or conditions) in this specification, unless otherwise indicated expressly or clearly in view of the context, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, a disclosure of a range is to be understood as specifically disclosing all values and further divided ranges within the range.

The terms "comprising", "including", and "having" are inclusive and therefore specify the presence of stated features, steps, operations, elements, or components, but do not preclude the presence or addition of one or more other features, steps, operations, elements, or components. Orders of steps, processes, and operations may be altered when possible, and additional or alternative steps may be employed. As used in this specification, the term "or" includes any one and all combinations of the associated listed items. The term "any of" is understood to include any possible combination of referenced items, including "any one of" the referenced items. The term "any of" is understood to include any possible combination of referenced claims of the appended claims, including "any one of" the referenced claims.

Features shown in one figure may be combined with, substituted for, or modified by, features shown in any of the figures. Unless stated otherwise, no features, elements, or limitations are mutually exclusive of any other features, elements, or limitations. Furthermore, no features, elements, or limitations are absolutely required for operation. Any specific configurations shown in the figures are illustrative only and the specific configurations shown are not limiting of the claims or the description.

Referring to FIG. 1, a monitoring device 10 is illustrated. The monitoring device 10 includes a plurality of openings 102, one or more buttons 104*a* and 104*b*, a plurality of slots 106, a visual indicator 108, a fan (internal fan) 109, and a housing 110. The housing 110 may include an outer peripheral wall 110*a*. The housing 110 may include a first (top) surface 110*b* and a second (bottom) surface (not shown) opposite the first surface 110*b*. The plurality of openings 102 may be disposed on the outer peripheral wall of the housing 110. The plurality of openings 102 may disposed in one or more columns and rows on the outer peripheral wall 110*a*. In an example, the plurality of openings 102 are arranged in four columns and three rows. It is contemplated that the plurality of openings 102 may be arranged in any suitable pattern for providing a desired level of airflow. The plurality of openings 102 may assist in airflow of the monitoring device 10.

The one or more buttons 104*a* and 104*b* may be disposed on the first surface 110*b* of the housing 110. The one or more buttons 104*a* and 104*b* may be a depressible button. The one or more buttons 104*a* and 104*b* may be used to identify one or more users of the monitoring device 10. For example, a first user may program biometric data into a user interface associated with the monitoring device 10 such that one of the buttons, 104*a*, indicates the monitoring device 10 is in use by the first user, as will be described in further detail below. As another example, a second user may program biometric data into the user interface associated with the monitoring device 10 such that the other of the buttons, 104*b*, indicates the monitoring device 10 is in use by the second user, as will be described in further detail below.

While in use, the slots 106 allow air to flow through housing 110 of the monitoring device 10. The slots 106 allow for the fan 109 of the monitoring device 10 to bring air into interior portions of the monitoring device 10. In an example, the slots 106 are disposed in a circular pattern. The slots 106 may be disposed noncontiguously in a circumferential direction of the circular pattern. The fan 109 may be disposed within an interior cavity of the housing 110. In an example, the monitoring device 10 includes only one fan 109, but it is contemplated that any number of fans 109 may be used to draw air into the monitoring device 10. As will be described in greater detail below, the air brought into the monitoring device 10 is measured by a sensor 20.

The visual indicator 108 may be disposed on the first surface 110*b* of the housing 110. The visual indicator 108 may be a light or any other means to visually indicate information related to the monitoring device 10. The visual indicator 108 may alert the user to information regarding the monitoring device 10. This information may be, for example, that 1) the monitoring device 10 is in use; 2) the monitoring device 10 is low on battery; 3) the monitoring device 10 is connected to Bluetooth™; 4) the monitoring device 10 is connected to WiFi; and/or 5) the monitoring device 10 is powered off.

Figure 2:
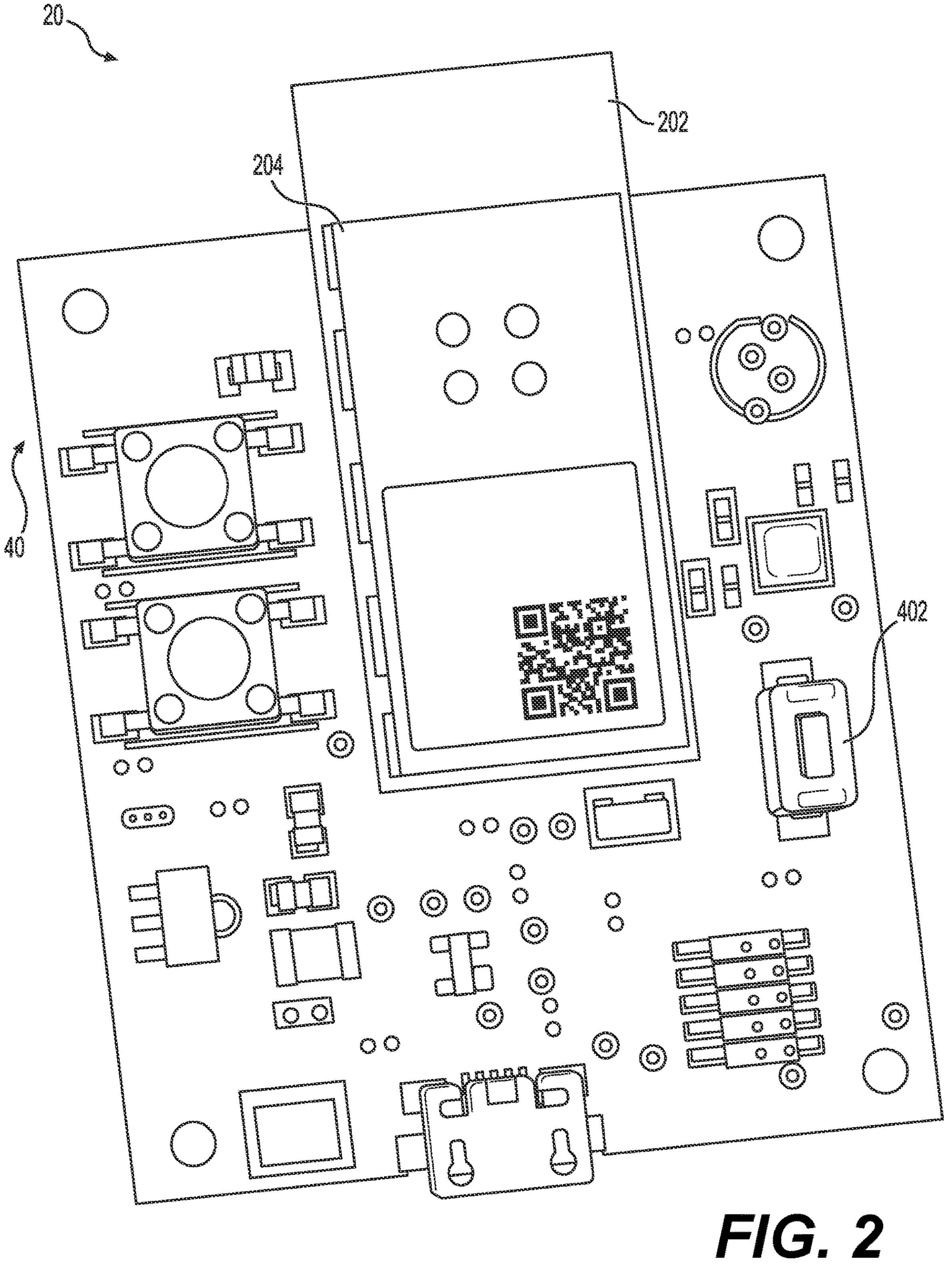
FIG. 2 illustrates a printed circuit board of the monitoring device of FIG. 1.

Referring to FIG. 2, the sensor 20 may include a film 202, a metal oxide layer 204, and a printed circuit board (PCB) 40. The metal oxide layer 204 may be disposed on the film 202. The metal oxide layer 204 may alter the resistance of the film 202. The metal oxide layer 204 may include any material that is semiconductive and suitable for reacting with gas molecules to dissociate into charged ions or complexes that alter resistance. The PCB 40 may also include a communication terminal 402. The communication terminal 402 may include a WiFi chip or any other suitable means (i.e., transmitting data using Bluetooth™ to a Bluetooth™ enabled device) for transmitting data gathered from the sensor 20 of the monitoring device 10 to a means for data storage and analysis. The sensor 20 and the PCB 40 may be disposed within the housing 110.

Figure 3:
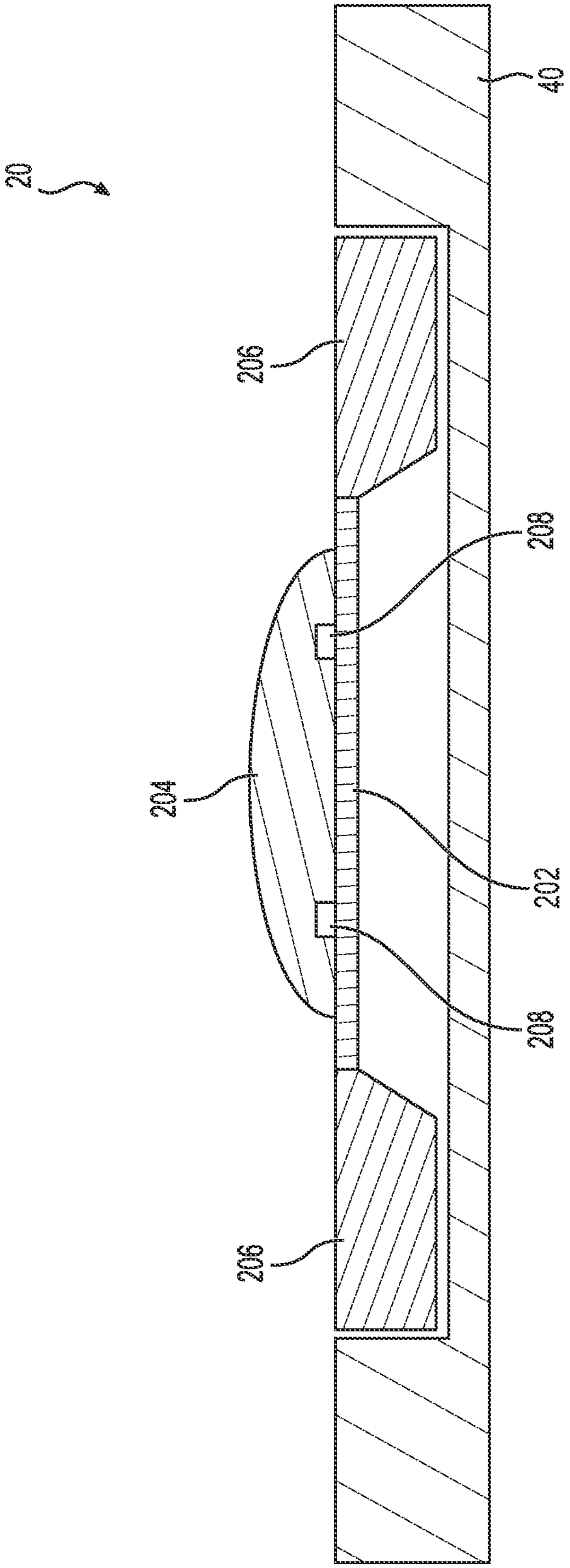
FIG. 3 illustrates a cross-sectional view of the printed circuit board of FIG. 2.

Referring to FIG. 3, the sensor 20 may further include a support plate 206, and a resistance gauge 208. The support plate 206 may be attached to the film 202 such that a space is formed between the film 202 and the PCB 40. This may result in the sensor 20 being disposed in a plane that is vertically offset from a plane of the PCB As will be described in greater detail below, the sensor 20 may measure the change in the resistance of the film 202 via the resistance gauge 208 and output the data to one or more users of the monitoring device 10.

Figure 4:
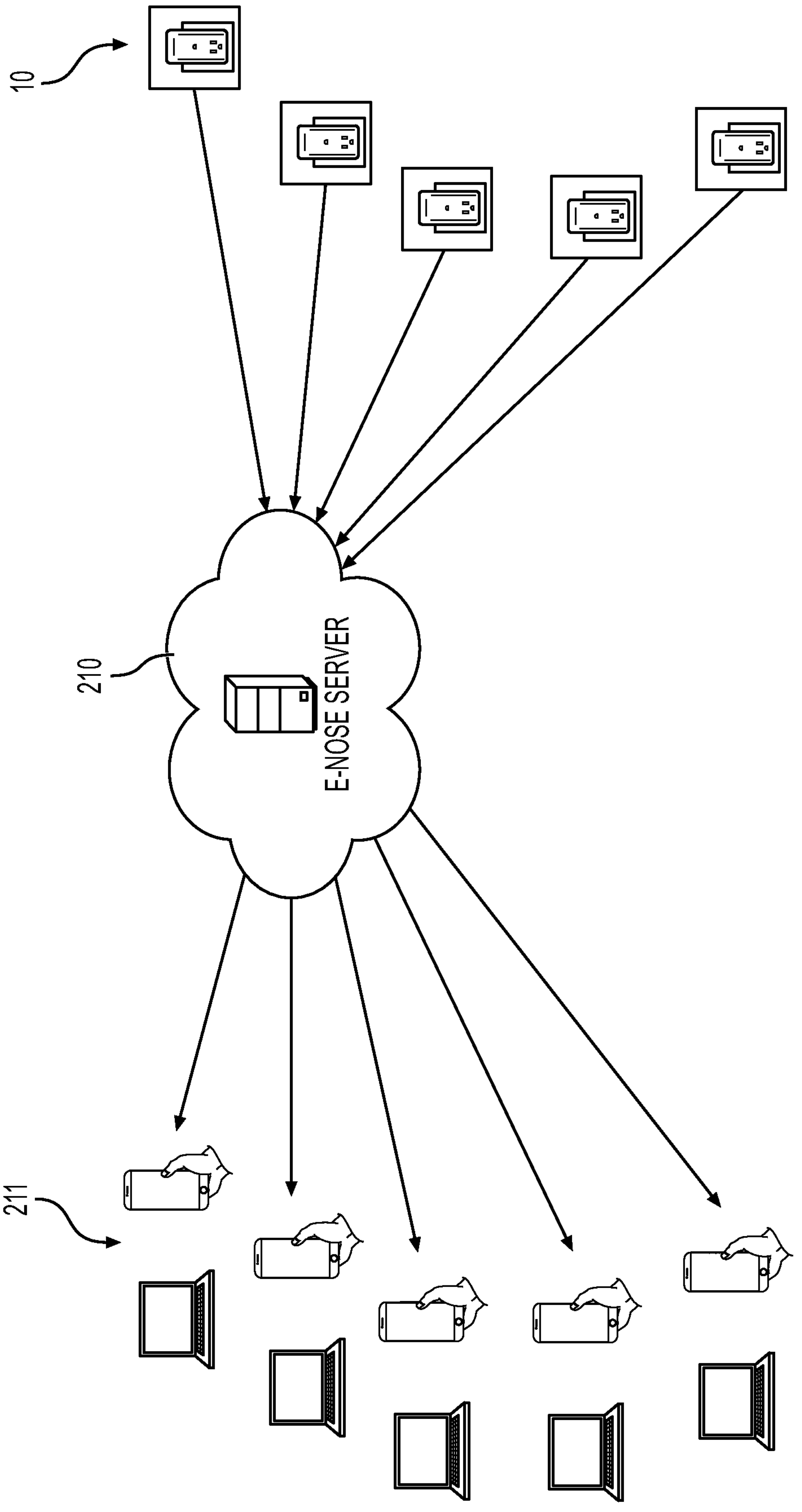
FIG. 4 illustrates a block diagram of an exemplary computing system that may perform the steps disclosed herein.
Figure 5:
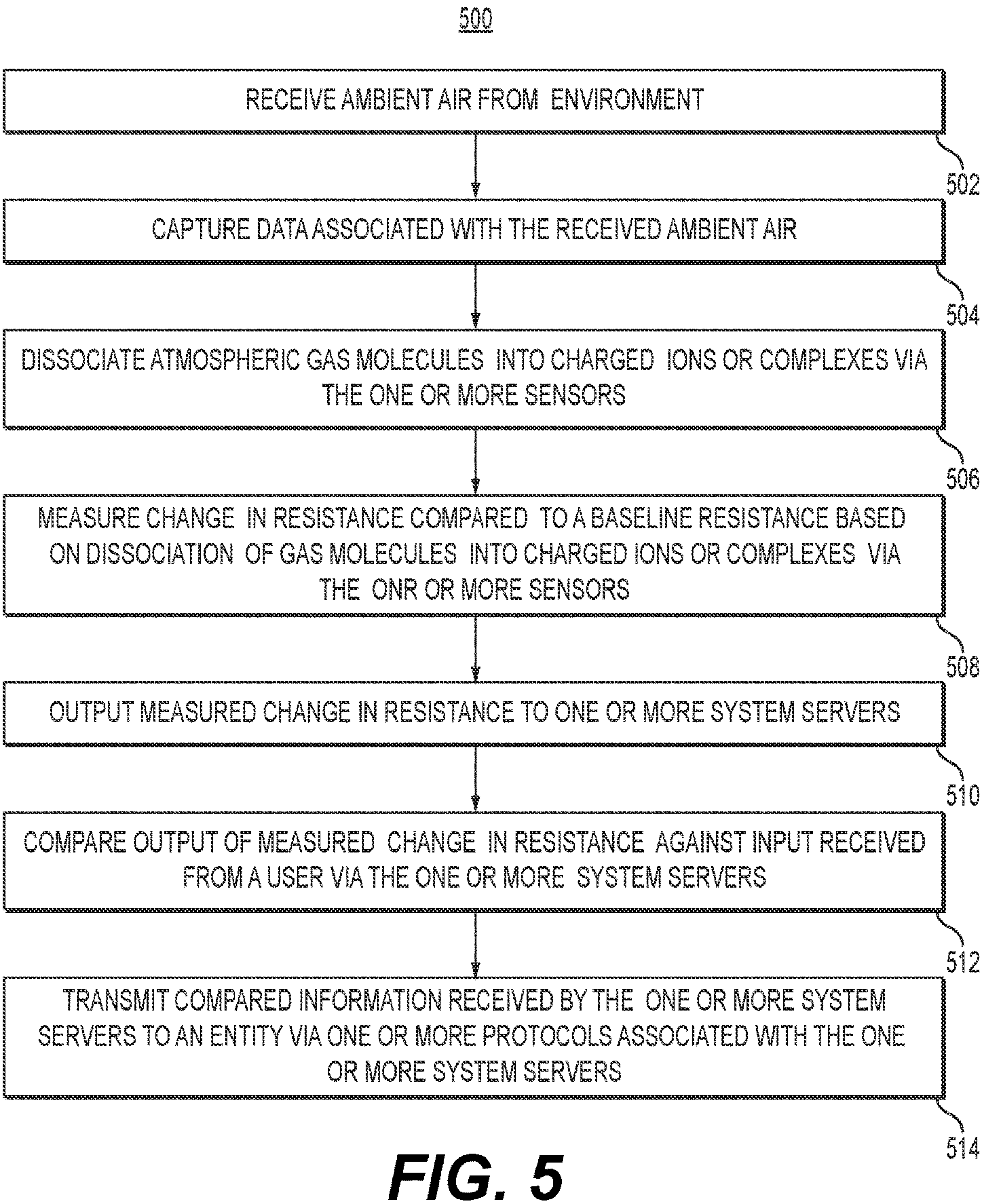
FIG. 5 illustrates a flowchart for an exemplary method of monitoring various organic compounds.

Referring to FIGS. 4 and 5, the monitoring device 10 may output the data received about the ambient air to a server 210. The server 210 may be in communication with one or more user devices 211.

FIG. 5 depicts a method 500 for measuring organic compounds. At step 502, the sensor 10 receives ambient air from the environment via the fan 108. The sensor 10 is placed in a desired location in which air is to be received. In an example, the monitoring device 10 is placed in a bathroom where the ambient air includes VOCs. In another example, the monitoring device 10 is coupled with an enclosed bowl. The ambient air may include, but is not limited to: vaporization of the contents in the stool, exhaled air from the user, toilet tissue, sweat vapors, or the like. The fan 108 may bring this air into the monitoring device 10 so that air flow can be maintained across the sensor 20. At step 504, the monitoring device 10 continuously captures data received from the sensor 20. This data may include VOCs, carbon dioxide, and/or any other byproduct emitting measurable organic compounds. At step 506, the sensor 20 dissociates gas molecules into charged ions or complexes that alter the resistance of the sensor 20 measured by the resistance gauge 208.

Figure 6:
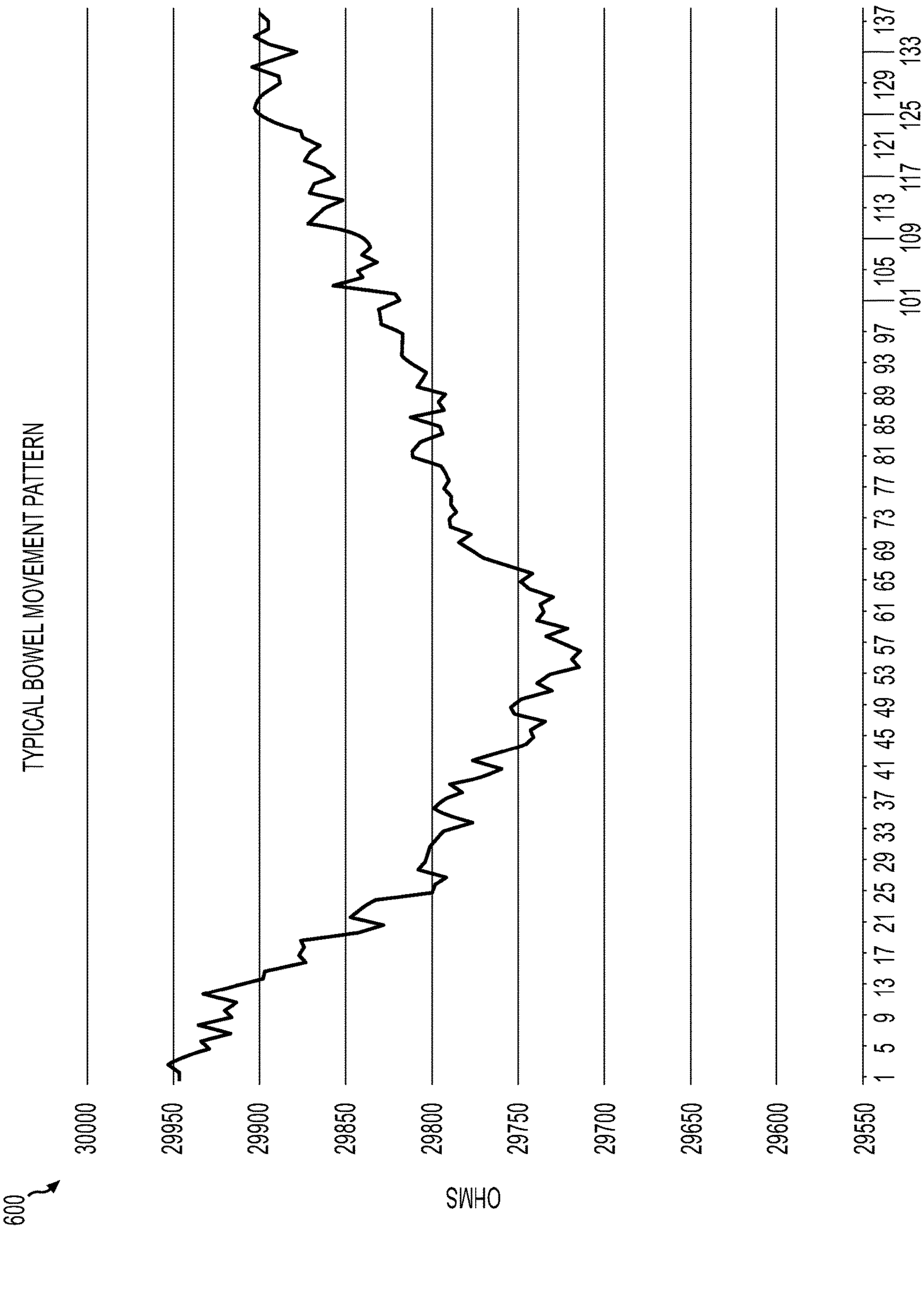
FIG. 6 illustrates a graph representing a typical bowel movement pattern according to the disclosure herein.
Figure 7:
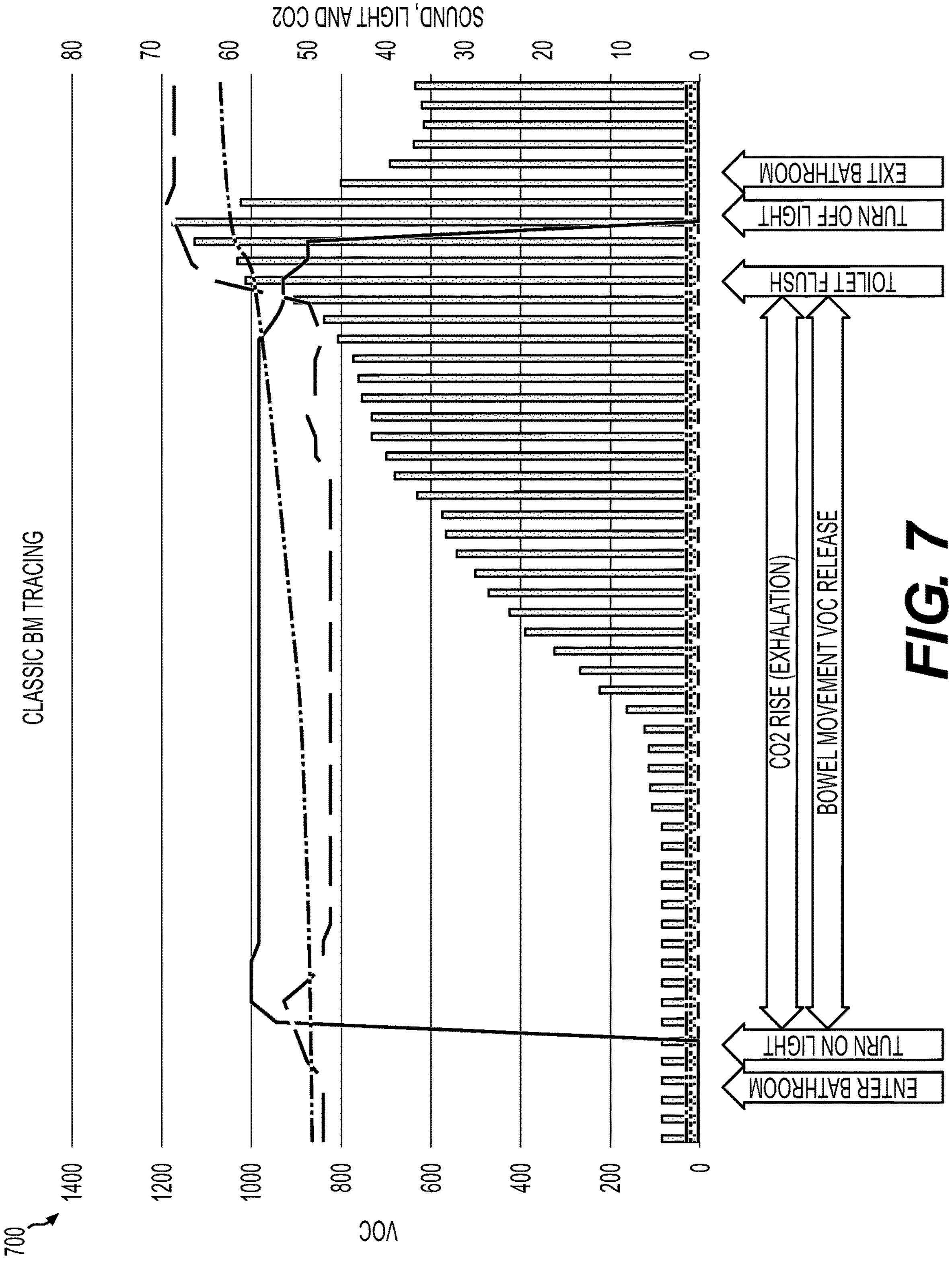
FIG. 7 illustrates a graph representing a measure of organic compounds in an environment according to the disclosure herein.
Figure 8:
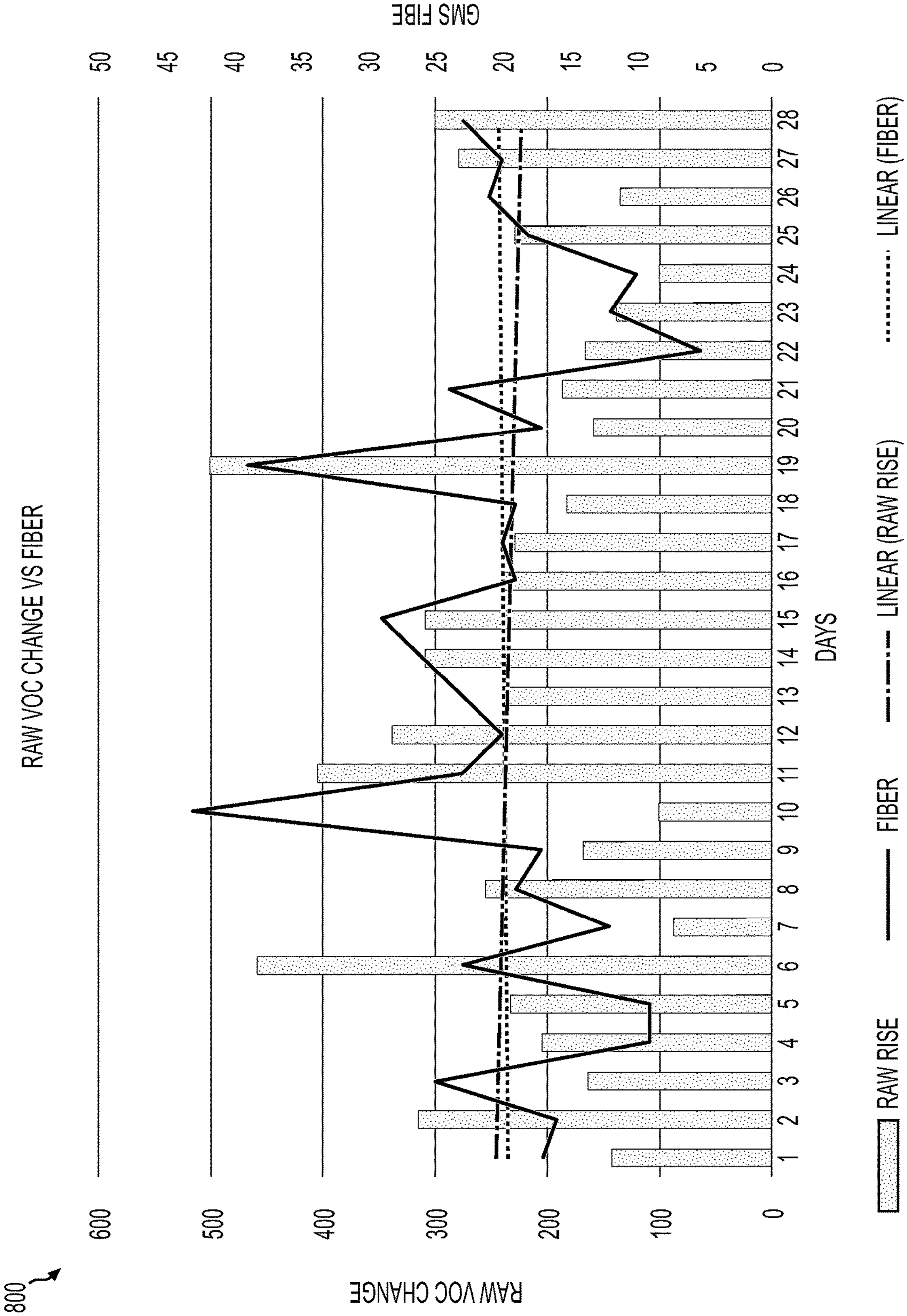
FIG. 8 illustrates a graph representing a comparison of organic compound change against fiber intake according to the disclosure herein.

At step 508, the change in resistance is compared to a baseline level of resistance correlated to an input received from the user via a system server resulting in an overall decrease in the resistance, illustrated in FIG. 6. The degree of fall as well as the duration of the fall are indicative of the amount of SCFAs and other products of fermentation present in the air. The inverse of this fall in resistance can be calculated, which correlates directly with the amount of SCFAs and other products of fermentation present in the air, illustrated in FIG. 7. At step 510, this change in resistance is output to server 210 of a downstream entity and at step 512, the change is compared against input data received at the server by the user, illustrated in FIG. 8. At step 514, the compared information is analyzed at the server 210 and transmitted to a device 211 of the user via Wi-Fi, Bluetooth™, or direct cable. The analyzed data may be transmitted in the form of a dietary recommendation. In some examples, protocols are used to create dietary recommendations back to the user and/or to the user's medical provider. In these examples, the protocol driven responses are automated based on the output of the monitoring device 10 and the specific protocol.

Figure 9:
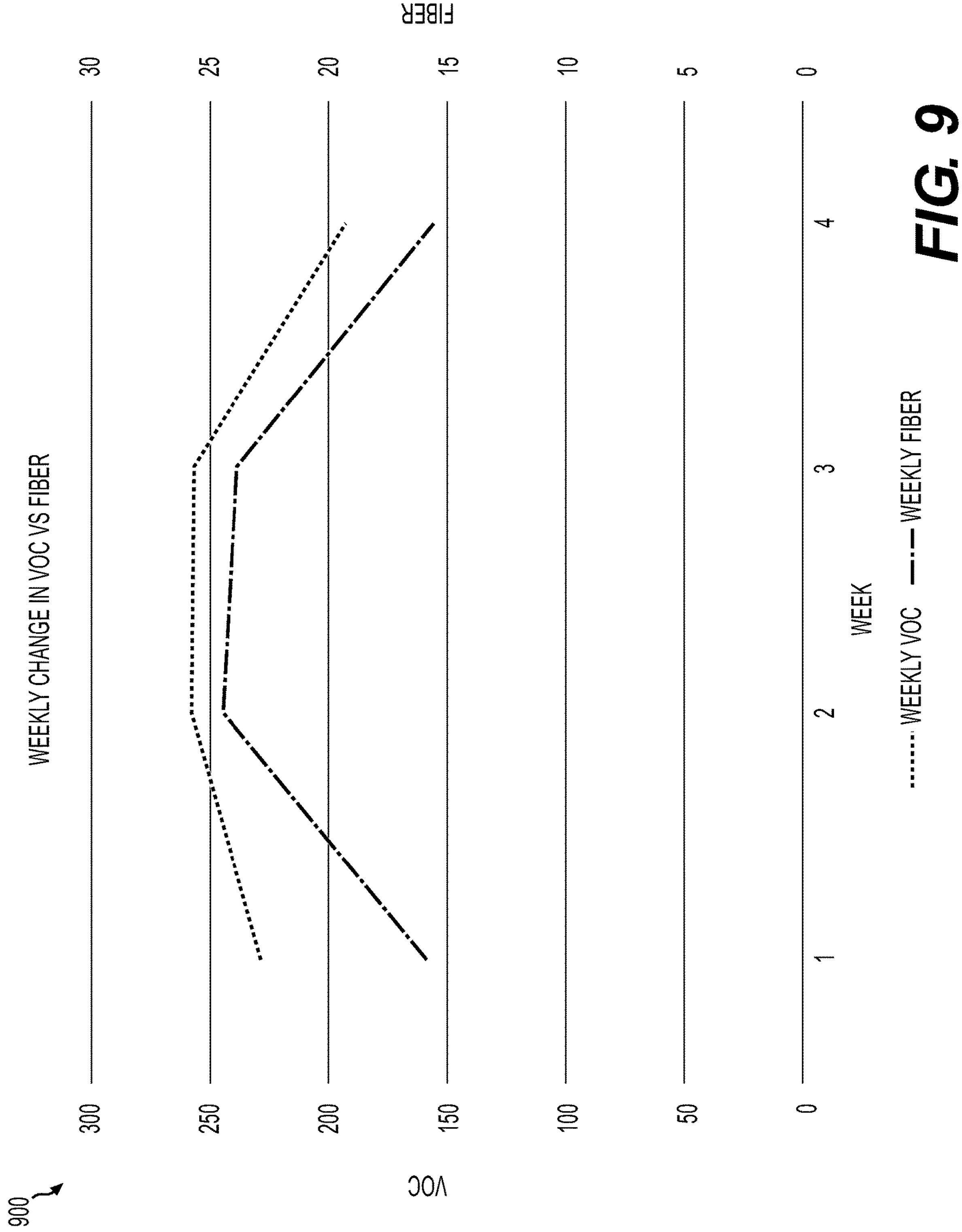
FIG. 9 illustrates a graph representing a comparison of organic compound change against fiber intake over a length of time according to the disclosure herein.

As shown in FIG. 9, the resulting analyzed data may be averaged over a period of time, such as a week or the like. In some examples, the analyzed data may be averaged over a day, a month, a year, or any desired length of time.

Figure 10A:
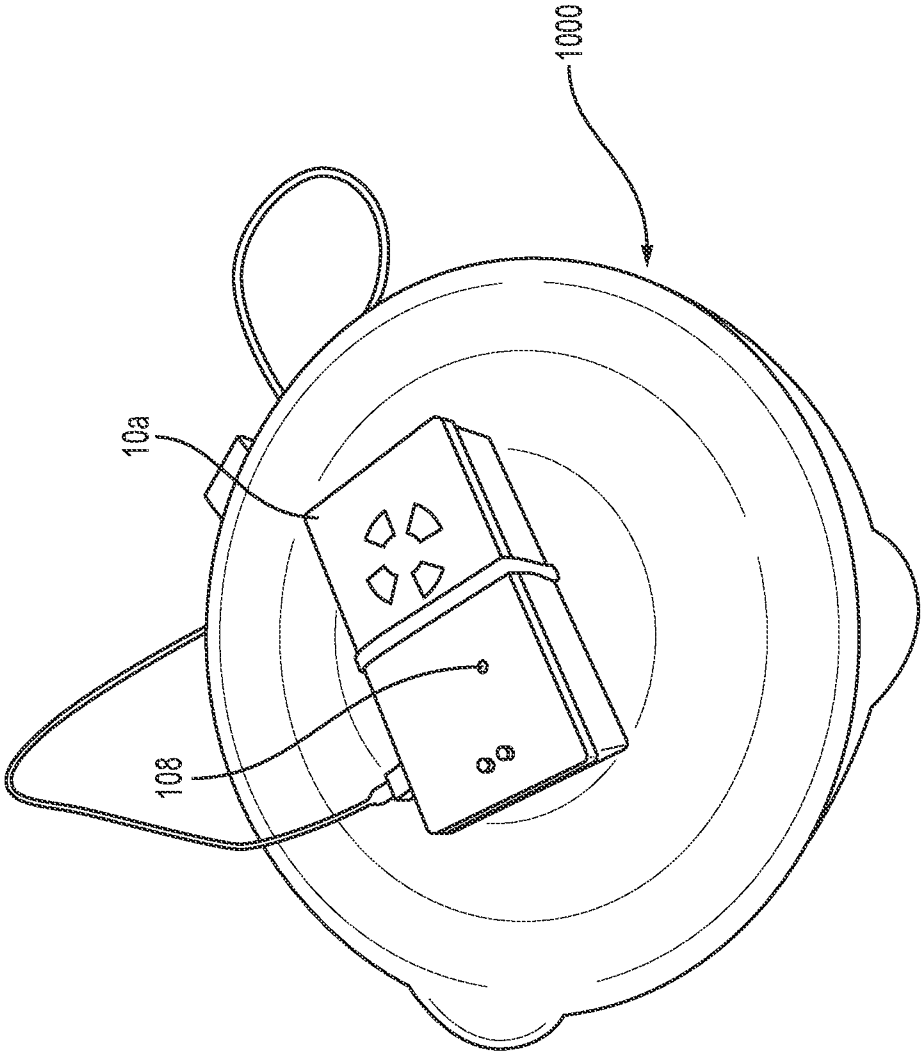
FIG. 10A illustrates an alternative embodiment of a monitoring device.
Figure 10B:
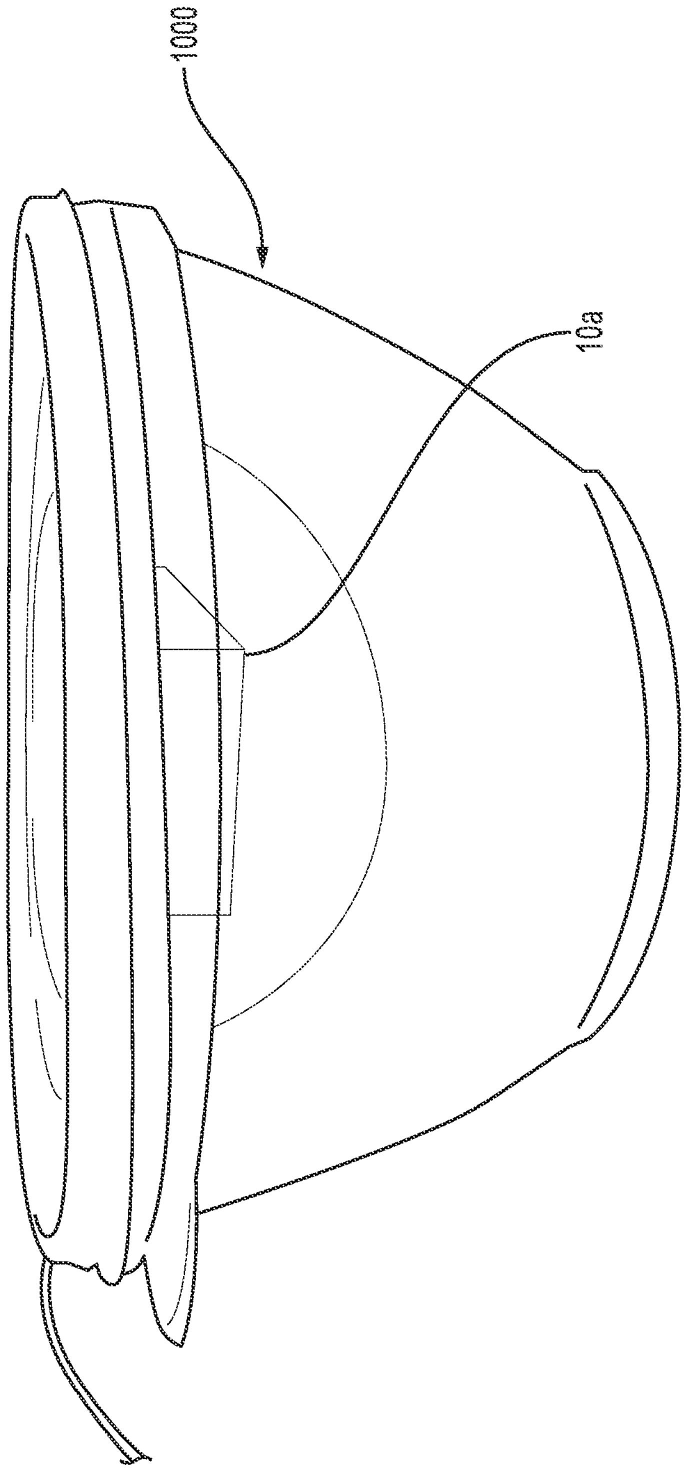
FIG. 10B illustrates the alternative embodiment of the monitoring device of FIG. 10A.
Figure 11:
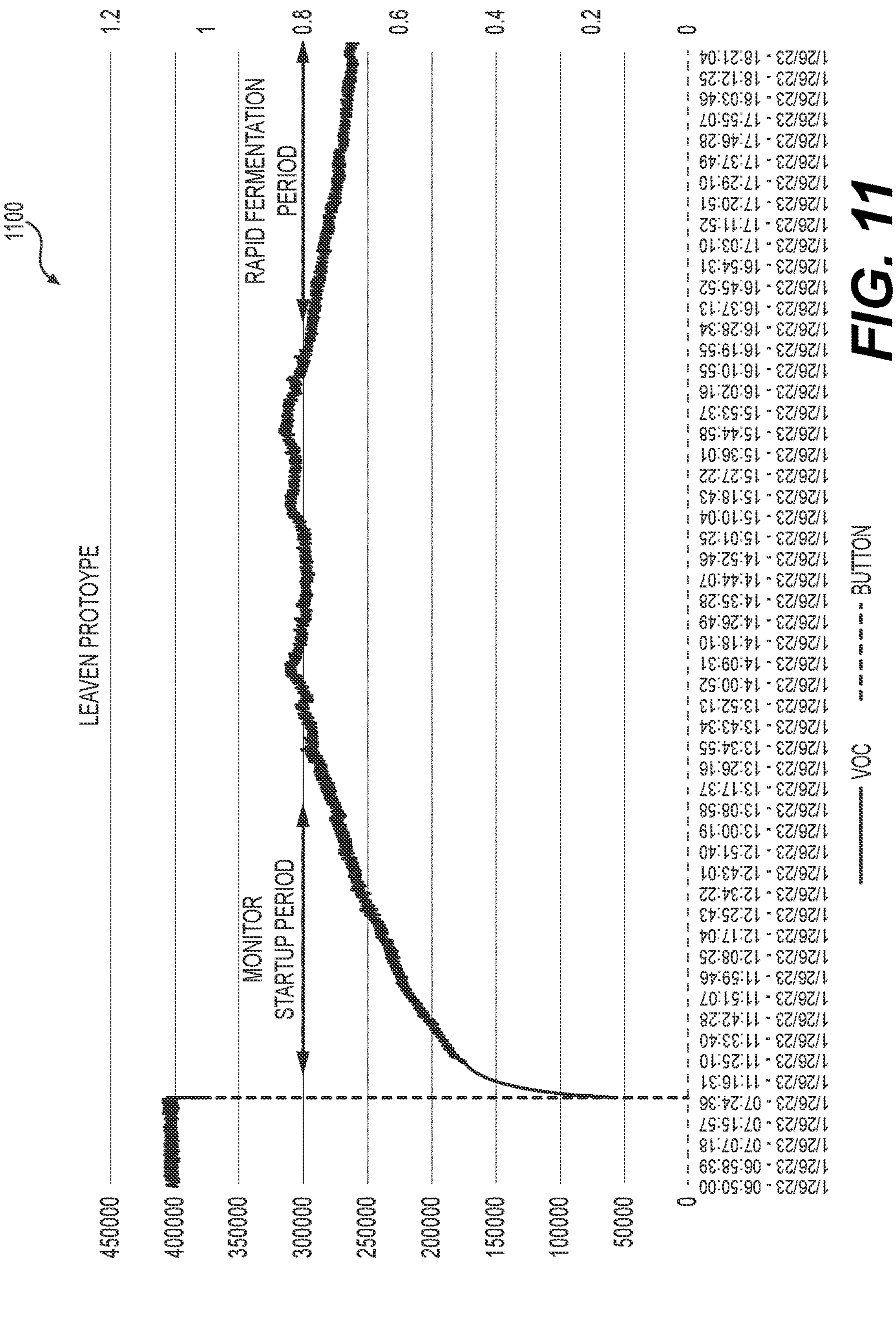
FIG. 11 illustrates a graph representing a comparison of when peak fermentation has occurred for both CO2 and VOCs.

As shown in FIGS. 10A and 10B, a monitoring device 10*a* may be incorporated into a leaven bowl 1000. The monitoring device 10*a* is substantially similar to monitoring device 10 except it may be smaller in overall dimension than monitoring device 10. Like reference numerals are used to refer to the same portions of monitoring device 10*a* as monitoring device 10. The monitoring device 10*a* may allow a user to be informed when peak fermentation has occurred for both CO2 and VOCs (as represented in FIG. 11). To facilitate this, when the microbiome in the leaven reaches peak fermentation, the visual indicator 108 on the monitoring device 10*a* may indicate that the leaven is ready by, for example, changing color (as shown in FIG. 10B). In some examples, a user may be notified that the leaven is ready via a user device.

As will be discussed herein, there are many embodiments in which this disclosure may be utilized. They are all based on the disclosure's nutritional monitoring through the detection of fecal VOCs derived from the fermentation of fiber. Dietary fiber is defined by the Institute of Medicine Food Nutrition Board as "nondigestible carbohydrates and lignin that are intrinsic and intact in plants." Higher intakes of dietary fiber reduce the risk of developing several chronic diseases, including cardiovascular disease, type 2 diabetes, and some cancers, and have been associated with lower body weights. These will be the basis for the embodiments for this disclosure. The Adequate Intake for fiber is 14 g total fiber per 1,000 kcal, or 25 g for adult women and 38 g for adult men, based on research demonstrating protection against coronary heart disease. Properties of dietary fiber, such as fermentability and viscosity, are thought to be important parameters influencing the risk of disease. Plant components associated with dietary fiber may also contribute to reduced disease risk. The mean intake of dietary fiber in the United States is 17 g/day with only 5% of the population meeting the Adequate Intake.

Fiber represents the nonabsorbable or poorly absorbable carbohydrate material contained in our diet, typically obtained from eating greens, grains, fruit and legumes. Their absorption is difficult because the body's enzyme systems are unable to break down the crystalline structure of these complex carbohydrates. They pass through the intestine undigested into the colon where they come in contact with the fecal microbiome, the trillions of bacteria and other microscopic organisms that inhabit it. Some of these organisms do have the ability to digest some of the complex carbohydrates by breaking them down to simple sugars which can then be metabolized into energy producing components for them. These are called soluble fiber. The remaining nonabsorbable fiber is referred to as insoluble.

The byproducts of the metabolism of soluble fiber are short chain fatty acids (SCFAs) and gasses like Hydrogen and Methane, which are not utilized by the microbiome, but rather are their waste. They have multiple functions, becoming food for the colon lining cells and are also absorbed into the circulation where they have systemic effects on metabolism. Some of them pass into the stool unchanged and become the inputs for this disclosure.

SCFAs protect us from cancer as well. One example is colon cancer, the second leading cause of cancer related deaths worldwide. Although some people are genetically predisposed to develop colon cancer, 70-90% of disease risk is attributable to environmental factors—most notably diets that are low in fiber and high in red meat. It is indisputable today that individuals with CRC have a different microbiome composition relative to healthy controls, referred to as dysbiosis. These patients have higher detectable populations of *Fusobacterium nucleatum* and decreased populations of protective bacteria like Rosburia and others. Recently published data have identified 29 specific bacterial species in the microbiomes of patients with CRC bringing us close to being able to define a "CRC microbiome."

SCFAs produced by the microbiome decrease the formation of colon cancer. One of the main SCFAs, Butyrate, is a well-known inhibitor of cell growth which makes it a preventive agent for the avoidance of cancer.

SCFAs, specifically Butryate, have the ability to control different cellular processes. To accomplish this, they use a process called epigenetic modification. The double helix of DNA was described by biologist James Watson and English physicist Francis Crick in 1953. Although we always see it described this way, DNA doesn't actually exist free in this state. This would be too dangerous. DNA needs to be protected because when DNA is damaged, cancers develop.

To protect it, DNA is wrapped in a protein complex called Chromatin, which keeps it more compact and protects it from being damaged. The primary protein components of chromatin are called histones, which bind to DNA and function as "anchors" around which the strands are wound. By stabilizing DNA, histones result in a lower incidence of colon cancer. Unlike normal colonocytes that use SCFAs as their primary energy source, cancer cells use glucose as their primary energy source. Since the cancer cells are not using the SCFAs, their concentration builds up in the cancer cell. One of the features of SCFAs is that they stabilize the histones in the chromatin, thus protecting the DNA within. The chemical process through which this occurs is called the Warburg Effect and it results in growth of normal colon cells and suppression of the cancer cell.

More evidence for the protective effect of SCFAs against colon cancer comes from investigations of mice who lack a receptor on their colonocytes for SCFAs. Cells need to use a transport protein to get SCFAs across their cell membranes so that they can enter their cells. Some people lack the receptor necessary for this and cannot transport SCFAs into their colonocytes as effectively. As a result, the tight junctions between the colonocytes are weaker and bacteria can enter the subepithelial tissues leading to inflammation, which leads to an increased incidence of cancers.

Finally, the mucous barrier is also protective against the development of CRC and its thickness is influenced by the microbiome. Mice deficient in mucin, lack an intact mucous barrier and spontaneously develop inflammation-driven CRC. Diet drives the development of the colonic mucous layer. Low-fiber diets have been shown to promote the expansion of mucous-degrading bacteria that can cause erosions of the intestinal barrier.

Therefore, a diet high in soluble fiber produced a SCFA-rich environment which decreases the incidence of colon cancer. Today, 25% of the adult population is at risk for the development of colon cancer and 6% ultimately do develop it. If their diet can be controlled and monitored for the intake of soluble fiber through the monitoring of fecal SCFAs, Colon Cancer incidence should decline.

The daily production of SCFAs through their release in the stool, which is measured as VOC, may be monitored by the monitoring device 10. SCFAs have an effect on our immune system at the cellular level which function to "throttle back" overactivity. This is accomplished through their effect on Dendritic Cells which are immune cells present in the lining of the gut. Dendritic Cells function as messengers that detect invaders and then migrate to lymph nodes where they activate immune cells called helper T-Cells, which are responsible for control of the infection. SCFAs like butyrate modulate the activity of Dendritic Cells. Although the effect of SCFAs doesn't interfere with control of infection, it does control overactivity that is present in Inflammatory Bowel Disease (IBD) and other chronic inflammatory disease like Rheumatoid Arthritis, Systemic Lupus Erythematosis and Psoriasis.

SCFA levels have been shown to decline in states of active IBD and rise again following effective therapy with Anti-TNF biologics. Diet therapy for IBD has very definite positive benefits on the health system. The incidence of IBD is increasing in the United States. Current treatment regimens are very expensive and can lead to immunosuppression, which can result in increased risk for infection and the development of hematologic malignancies. As a result, many patients and their providers want nonpharmacologic approaches for managing their disease. An estimated 80% to 89% of patients want their physicians to provide dietary advice.

A cross-over study of patients with IBD in remission found that a catered low-fat, high-fiber diet decreased markers of inflammation and reduced intestinal dysbiosis in fecal samples. This disclosure may detect the presence of the byproducts of fiber fermentation including SCFAs. The monitoring device 10 may therefore be used as a means of monitoring the clinical status of patients with IBD even in the absence of symptoms. This is critical since the ultimate control of IBD resides in the ability to control inflammation.

Patients with Crohn's disease whose median intake of fiber was 23.7 g per day were 40% less likely to experience a flare as compared with those whose median consumption was 10.4 g of fiber per day. Only through tight control of inflammation can we control the course of these diseases. This disclosure through its ability to monitor SCFA VOC activity can be used to maintain patients on the high-fiber diet necessary to control their IBD.

Type 2 diabetes currently affects 20% of the US population. In addition to those who are known to have diabetes, there is almost an equally sized population of Americans who have pre-diabetes. The main reason for the high incidence of diabetes is the high prevalence of overweight and obese American. Diabetes is caused by a lack of insulin, the protein necessary to move sugar from the bloodstream into our cells. When we don't have enough insulin, our blood sugar rises and we suffer the complications of diabetes.

There are two types of diabetes, type one and type two. Type one diabetes is typically a disease of the young who totally lose their ability to produce insulin. Only about 20% of diabetics have type one diabetes. 80% have type two diabetes (T2D). Patients with T2D actually produce more insulin than non-diabetic people. The problem is that the insulin they produce doesn't work. They have what is called "insulin resistance". This is directly related to the fact that they are overweight or obese. Excess fat causes hormonal changes that result in insulin resistance.

SCFAs, specifically butyrate has been shown to cause stimulation of a small intestinal hormone called Glucagon-Like-Peptide-1 (GLP-1), which results in increased glucose transfer out of the bloodstream into fat and muscle cells, increased production of insulin by the pancreas, and increased oxidation of fat by the liver. This all improves insulin sensitivity, thus decreasing insulin resistance. It also decreases appetite. What a wonderful combination of effects, all from eating more fiber. Thus, the disclosure, with its ability to detect the presence of products of SCFA fermentation in the stool can promote the ingestion of a diet that will help control type 2 diabetes.

Nonalcoholic fatty liver disease (NAFLD) currently affects 25% of the adult world population. 20% of the people with NAFLD (5% of the population) also have a progressive fibrosis of the liver called Nonalcoholic Steatohepatitis (NASH). This progressive disease is now the most common reason for liver transplantation in the US and a major cause for liver cancer. It is estimated that 46.9% of patients with NAFLD will progress to NASH.

Preclinical studies have provided the strongest evidence for a causal role of the gut microbiome in NAFLD. Several pivotal studies established that mice lacking gut microbiota are resistant to the development of diet-induced hepatic steatosis and that hepatic steatosis is both transmissible via fecal microbiota transplantation (FMT) and ameliorated by probiotics and antibiotics in murine models. Given this compelling preclinical evidence, the gut-liver axis is a rapidly developing area of investigation and new insights are emerging from a growing number of human studies.

The liver is the first organ to receive the output from the intestine through the portal circulation, so it is vulnerable to whatever contents are passed to it by the intestine. The lining cells of the small intestine and colon possess tight junctions between cells. This maintains an effective barrier to the passage of intestinal contents to the circulation and on to the liver. The tight junctions between the cells lining the intestine have been found to be disrupted in the dysbiosis of patients with NAFLD and NASH. Intestinal epithelial barrier disruption leads to increased translocation of harmful microbial products, such as lipopolysaccharide and endotoxin into the portal circulation which results in endotoxemia that can induce hepatic inflammation.

SCFAs exert broad biological activities including the promoting fatty acid oxidation, resolving inflammatory responses, modifying host caloric intake, and maintaining the gastrointestinal epithelial barrier. Although the precise role of SCFAs in NAFLD remains uncertain, clinical models of NAFLD report decreased SCFA abundance. Supplementation of SCFAs improves diet-induced hepatic steatosis in murine models; however, in contrast to these findings, human studies have noted increased fecal concentrations of SCFAs in adults with NAFLD. Therefore, this disclosure has a role in maintaining the patient on a diet that is conducive to maintenance of the tight junctions and therefore decreasing the inflammatory activity of both NAFLD and NASH.

Some of the SCFAs and other compounds produced by the fecal microbiome are absorbed into the bloodstream and are carried to distant sites in the body. They then travel to the brain where they can affect cognitive abilities through a gut-brain cross talk. Metabolites of microbiome fermentation, such as SCFAs, and more specifically butyrate, have the ability to prevent degeneration in the brain. SCFAs also have an impact on the blood brain barrier which keeps harmful chemicals out of the brain. It's a protective barrier for brain cells. SCFAs improve the tightness of the blood brain barrier. There is also growing evidence that extensive communications exist between the brain and the gut via the gut-brain axis, which is composed of the central nervous system and the gut (enteric) nervous system. Through these connections it can affect appetite and eating behavior.

Parkinson's disease (PD) is the second most common neurodegenerative disease, after Alzheimer disease. It is also the fastest growing neurologic disease, and may have its origins in the gut. The integrity of the intestinal mucosal barrier is maintained by specific contribution from the lining epithelial cells, including enteroendocrine cells, the enteric nervous system, immune cells and the fecal microbiome. Aging and exposure to environmental toxins are risk factors for Parkinson's disease and are associated with impaired mucosal barrier function, the microbiome and its products, as well as ingested toxins. A "leaky" gut facilitates entry of luminal microbes and their products as well as ingested toxins into the systemic circulation. This triggers activation of resident immune cells and inflammation, which disrupt enteric neuronal and glial function, which can lead to damage in enteric neurons and neurodegeneration. In this manner, age, environment, diet, and toxins may affect the induction, pathogenesis, and rate of disease progression.

Diets high in fiber producing large amounts of SCFAs have been shown to improve the intestinal barrier in NAFLD and NASH. This same diet can function to improve the intestinal barrier in Parkinson's disease. This disclosure can monitor patient compliance with a high-fiber diet which will improve the status of patients with these degenerative CNS diseases.

Further, dietary therapy has been the mainstay in the treatment of obesity, but interindividual results are quite variable and even when there are successes, the long-term maintenance of weight loss typically fails and weight is regained. It has been shown that the gut microbiota is essential for the immediate personal dietary response to glycemic challenges. The gut microbiota is gaining recognition as a metabolic organ integrated into the host's metabolic network. The obese phenotype is transmissible through fecal microbiota transplantation, suggesting the relevance of the gut microbiota in fat deposition. A well-functioning gut microbiota consists of multiple commensal microorganisms with diverse functions, which may directly contribute to the energy balance by fermentation of dietary fibers and regulate the energy equilibrium through bioconversion of dietary components into metabolically bioactive molecules. Given its association with metabolic diseases and its involvement in host metabolism, the gut microbiota can provide information on the host's metabolic status.

SCFAs, specifically butyrate, improve mitochondrial function increasing metabolic rate and caloric consumption. This has anti-diabetic and anti-obesity effects. Butyrate also has positive effects on mitochondria in the brain and the liver. A high fiber diet promotes the growth of the families of bacteria that produce large amounts of butyrate which then feeds the colon and stimulates mitochondria throughout the body.

The baseline microbiota structure is a potential stratification factor, distinguishing the weight loss effects of certain dietary factors, where, for instance, fiber intake seems to be a factor benefiting weight loss in some, but not all individuals. A personalized weight prediction model can be built based on baseline gut microbiota composition and dietary data. This disclosure may to provide a personalized profile for weight reduction based upon the individual's ability to generate VOCs. This profile can then be altered through adherence to a high-fiber diet which will over time improve the individual's ability to lose weight and maintain this weight loss.

Cardiometabolic diseases (CMDs), such as hypertension, atherosclerosis and coronary artery disease, are part of a spectrum of diseases with shared causes and features. CMDs can be initiated by a Western lifestyle characterized by insufficient physical activity and high caloric intake. This high caloric intake results in obesity and low-grade inflammation, which often precedes cardiovascular disease (CVD).

Because a Western diet is a major risk factor for CMDs, dietary aspects are important for cardiometabolic health. However, diet can also improve CMD, as the Mediterranean diet can improve cardiovascular health as well as prevent and treat diabetes. In addition to this, studies suggest that a high intake of fibers, which are degraded by gut microbiota (GM) to short-chain fatty acids (SCFA), is associated with insulin sensitivity. The GM has also been shown to influence host metabolism. Feces transplantation from lean donors to individuals with metabolic syndrome improved insulin sensitivity and increased the abundance of bacteria that produce the SCFA butyrate. In fact, microbiota-derived metabolites have been shown to be associated with properties of CMDs. In addition, the microbiota-derived metabolite trimethylamine N-oxide from dietary choline and phosphatidylcholine is associated with CVD. This suggests that diet indirectly modulates clinical parameters of CMDs and the risk of developing CMDs through the GM. Overall, a Mediterranean and a low-fat high-fiber diet both improved insulin sensitivity and reduced plasma triglyceride levels.

Since dietary interventions modulating CMDs affect the GM composition and dietary interventions changing the GM also influence clinical parameters, such as diastolic blood pressure, in overall CMD, and a high-fiber diet decreased triglyceride levels in participants; this disclosure can occupy a significant position in the monitoring of patients placed on Mediterranean and High-fiber diets.

The maintenance of healthy bowel function requires regularity of bowel movement, which is dependent upon a regular intake of dietary fiber. Although patients can be placed on a high fiber diet, compliance is a constant issue. Through the use of monitoring device 10, users will be monitored and receive feedback on their compliance. This has disease ramifications in the form of the development of diverticular disease, Irritable Bowel Syndrome, Pelvic floor dyssynergia and Hemorrhoids.

Maintenance of normal regular bowel function relies on a consistent intake of nondigestible, insoluble fiber obtained from grains, greens and fruit. The reason for this is that a minimal degree of bulk must be maintained in the stool so that the propulsive forces of peristalsis can result in correct mixing and movement of the stool through the colon. If adequate fiber intake is not maintained, stool will mix poorly and will not move along the left side of the colon.

The colon is five feet long and surrounds the abdomen like a large question mark. It has two jobs, the first of which is to absorb water. Since the small intestine is not able to concentrate its contents, about a half-gallon of water enters the right side of the colon every day. This has to be absorbed back into our bodies or else we would suffer dehydration very easily. The colon reabsorbs this salty water very well.

The second job of the colon is to package the stool in a form that can be conveniently eliminated. The packaging process of stool is a complex one. When food enters the colon on the right side, its contents are that of a thin liquid. The absorption of the water is a continuous and progressive process as the stool courses around the five-foot colon towards the left side. The contents of the colon on the right side are liquid whereas they are solid on the left, which results in a different pressure situation on the right vs. the left side of the colon. Adequate insoluble fiber intake will promote normal passage of the stool through the left side of the colon resulting in normal bowel function. This disclosure may to monitor fiber intake through its generation of SCFAs and the VOCs that vaporize from them.

Diverticular disease, the presences of multiple thin-walled sacs in the wall of the colon is a very common condition. It is present in over 50% of US adults over the age of 50 and in the overwhelming majority of these individuals it is a silent process producing no symptoms. A colonic diverticulum is a pouchlike protrusion in which the inside lining of the colon wall herniates through the muscle layer surrounding it at points of weakness where blood vessels traverse the colon wall. These diverticuli can become inflamed usually due to a low fiber diet. When inflammation occurs, diverticulitis occurs. Rates of diverticulitis have been rising. Diets low in fiber have been associated with an increased risk of diverticulosis or diverticulitis. In the presence of a low fiber diet, stool particles may accumulate in diverticula, become inspissated and hardened, and erode through the diverticular wall. If a diverticulum perforates freely into the abdominal cavity, either diffuse peritonitis results or the leak is walled off into an abscess. These are very serious complications and require high dose antibiotics and often require surgery. Patients with diverticulosis therefore require lifelong maintenance of a high-fiber diet. This disclosure can assess the degree of fiber intake of each user and can be used to promote and maintain the individual on a high-fiber diet thus avoiding complications associated with diverticular disease.

Irritable Bowel Syndrome (IBS) is a chronic and somewhat disabling functional bowel disorder. IBS is diagnosed on the basis of recurrent abdominal pain related to bowel movements or in association with a change in stool frequency or form. Bloating is a common accompanying symptom. IBS negatively affects quality of life and work productivity. Many patients with IBS identify specific dietary triggers for their symptoms. Increasing dietary fiber intake is a traditional first-line treatment for patients with the constipated form of IBS, but insoluble fiber, such as bran, can exacerbate abdominal pain and bloating. A systematic review and meta-analysis of seven placebo-controlled trials, involving a total of 499 patients, showed that soluble fiber was beneficial in the management of IBS.

Defecatory disorders are most commonly due to dysfunction of the pelvic floor or anal sphincter. Failure of the rectum to empty effectively may be due to an inability to coordinate the abdominal, recto-anal, and pelvic-floor muscles during defecation. These dysfunctions can be identified clinically. Ignoring or suppressing the urge to defecate may contribute to the development of mild constipation before the evacuation disorder becomes severe. Slow-transit constipation occurs most commonly in young women who have infrequent bowel movements (once a week or fewer). The condition often starts at puberty. Associated symptoms are an infrequent urge to defecate, bloating, and abdominal pain or discomfort.

In individuals with a minimal delay in colonic transit, dietary factors contribute to symptoms. In these patients, a high-fiber diet may increase stool weight, decrease colon-transit time, and relieve constipation. This disclosure may monitor patients with pelvic floor dyssynergia for adherence to the appropriate high-fiber diet.

Hemorrhoids are collections of submucosal, fibrovascular, arteriovenous sinusoids that are part of the normal anorectum. The purpose of these "vascular cushions" is incompletely understood, but they appear to be important for sensing fullness and pressure and for perceiving anal contents. In addition, they may support anal closure, facilitate continence, and help protect the anal sphincter from injury during defecation.

All patients should be encouraged to ingest a sufficient amount of insoluble fiber and sufficient water to avoid constipation and straining and to limit the time spent on the toilet. A meta-analysis of controlled trials showed that fiber supplementation was associated with significant reductions in the risk of persistent symptoms and the risk of rectal bleeding. This disclosure may assist in the monitoring and control of diet in patients with hemorrhoids.

Further, in examples, the monitoring device 10 may be applied to bread baking, specifically using natural leavens is a delicate process that requires the monitoring of the degree of both fermentation as well as the level of VOC production. Sourdough bread has a unique depth of flavor in its crumb, which is derived from the balance of yeast fermentation of the sugars in flour and bacterial action on its gluten. Both of these characteristics are driven by the quality of the natural leaven used in the production of the bread. The product of yeast fermentation is CO2 gas whereas the product of bacterial enzymatic action is VOCs. Monitoring device 10 may measure both forms of fermentation.

Sourdough bread making is very difficult for the home baker as it relies on the creation of a living ecosystem of yeast and bacteria. Numerous variables (temperature, humidity, barometric pressure, etc.) interact to either promote the formation of a healthy ecosystem and flavorful bread or work to make it very difficult to create.

The stages in the creation of sourdough bread include: 1) formation of the Starter; 2) utilization of the Starter to create Leaven; 3) adding flour, water and salt to the Leaven; 4) bulk Fermentation; 5) shaping of the dough; 6) final Fermentation; 7) baking; and 8) cooling.

The monitoring device 10 may aid at steps: 1, 2, 4 and 6 by providing the baker with an accurate assessment of the amount of C02 and VOCs that have been produced. This data can then be used by the baker to determine their level of "sourness" in their bread. There are no current products available that have this ability.

Like bread baking, beer brewing involves the fermentation of starch-based material, commonly barley, through the action of yeast. To be successful, the brewer must create an environment where yeast can thrive and transform the starches in the malted barley into alcohol and flavor. To do so, brewers must carefully control variables such as temperature, pH, oxygenation, and ingredients. Each of these factors affects the overall composition of the finished product, thus, the monitoring device 10 or 10*a* may aid in this process.

The detailed description and the drawings or figures are supportive and descriptive of the present teachings, but the scope of the present teachings is defined solely by the claims. While some of the best modes and other embodiments for carrying out the present teachings have been described in detail, various alternative designs and embodiments exist for practicing the present teachings defined in the appended claims.

While various embodiments have been described, the description is intended to be exemplary, rather than limiting and it will be apparent to those of ordinary skill in the art that many more embodiments and implementations are possible that are within the scope of the embodiments. Any feature of any embodiment may be used in combination with or substituted for any other feature or element in any other embodiment unless specifically restricted. Accordingly, the embodiments are not to be restricted except in light of the attached claims and their equivalents. Also, various modifications and changes may be made within the scope of the attached claims. Benefits, other advantages, and solutions to problems, and any element or elements that may cause any benefit, advantage, or solution to occur or become more pronounced, however, are not to be construed as critical, required, or essential features or elements of any or all of the claims, unless such benefits, advantages, solutions, or elements are expressly stated in such claims.

What is claimed is:

1. A monitoring device for measuring volatile organic compounds present in ambient air surrounding the monitoring device, the monitoring device comprising:

a housing of the monitoring device, the housing defined by an outer peripheral wall, wherein the outer peripheral wall comprises at least a first surface and a second surface opposite the first surface, the second surface defining an interior cavity disposed within the housing;

a fan disposed within the interior cavity;

a plurality of slots in the outer peripheral wall, the plurality of slots disposed directly above the fan and operable to receive ambient air continually pulled from an environment outside of the housing into the interior cavity by the fan;

a visual indicator disposed on the first surface of the outer peripheral wall to indicated a status of the monitoring device;

one or more buttons disposed on the first surface of the outer peripheral wall, wherein each of the one or more buttons is operable to be independently selected by one or more unique users of a household;

a sensor that is disposed within the housing, the sensor comprising a film that is offset from a printed circuit board (PCB) by a support plate forming a space between the film and the PCB, wherein the sensor continually receives the ambient air including the volatile organic compounds and detects a change in resistance associated with a presence of volatile organic compounds in the ambient air; and a processor operatively coupled with the sensor and programmed with executable instructions that cause the processor to:

receive the detected change is resistance from the sensor as a measurement:

calculate the change in resistance over a period of time as ambient air is continually pulled into the interior cavity; and transmit, via a wireless transmitter operatively coupled with the processor, the calculated change in resistance over the period of time to a web server in electronic communication with the monitoring device over a network, wherein the web server compares the calculated change in resistance over the period of time to a baseline level of resistance associated with a unique user of the one or more unique users and determines a set of dietary recommendations associated with an intestinal microbiome of the unique user.

2. The monitoring device of claim 1, wherein the one or more buttons are configurable according to a user of the monitoring device.

3. The monitoring device of claim 1, wherein the film comprises a metal oxide layer.

4. The monitoring device of claim 3, wherein the metal oxide layer comprises a semiconductive material, and wherein the semiconductive material is configured to change a resistance of the sensor when exposed to the ambient air.

5. The monitoring device of claim 4, further comprising a resistance gauge configured to measure the change of the resistance of the sensor as the semiconductive material is exposed to the ambient air.

6. The monitoring device of claim 1, wherein the PCB comprises communications terminal, the communications terminal configured to communicate with a downstream entity via an electronic network.

7. The monitoring device of claim 1, further comprising a user interface configured to receive biometric data of a user to assign to the one or more buttons.

8. A monitoring device for measuring volatile organic compounds present in ambient air surround the monitoring device, the monitoring device comprising:

a housing of the monitoring device, the housing defined by an outer peripheral wall, wherein the outer peripheral wall comprises at least a first surface and a second surface opposite the first surface, the second surface defining an interior cavity disposed with the housing;

a fan disposed within the interior cavity;

a plurality of slots in the outer peripheral wall, the plurality of slots disposed directly above the fan and operable to receive ambient air continually pulled from an environment outside of the housing into the interior cavity by the fan;

one or more buttons disposed on the outer surface of the outer peripheral wall, wherein each of the one or more buttons is operable to be independently selected to indicate that the monitoring device is in use by a unique user;

a visual indication disposed on the first surface of the outer peripheral wall;

a sensor comprising:

a film comprising a metal oxide layer;

a printed circuit board (PCB) vertically offset from the film, wherein the PCB continually receives the ambient air including the volatile organic compounds, and wherein the sensor detects a change in resistance associated with a presence of the volatile organic compounds; and a support plate, wherein the support plate is affixed to the film such that a space is formed between the film and the PCB; and a processor operatively coupled with the sensor and programmed with executable instructions that cause the processor to:

receive the detected change in resistance from the sensor as a measurement:

calculate the change in resistance over a period of time as ambient air is continually pulled into the interior cavity; and transmit, via a wireless transmitter operatively coupled with the processor, the calculated change in resistance over the period of time to a web server in electronic communication with the monitoring device over a network, wherein the web server compares the calculated change in resistance over the period of time to a baseline level of resistance associated with the unique user and determines a set of dietary recommendations associated with an intestinal microbiome of the unique user.

9. The monitoring device of claim 8, the sensor further comprising:

a resistance gauge configured to measure a change in a resistance of the film as the film is exposed to the ambient air.

10. The monitoring device of claim 8, wherein the metal oxide layer is comprised of a semiconductive material configured to alter a resistance of gas molecules in the ambient air.

11. The monitoring device of claim 8, wherein the PCB comprises a communications terminal configured to communicate with a downstream entity via an electronic network.

12. The monitoring device of claim 8, wherein the volatile organic compounds include short chain fatty acids.

13. A monitoring device for measuring volatile organic compounds present in ambient air surrounding the monitoring device, the monitoring device comprising:

a housing of the monitoring device, the housing defined by an outer peripheral wall, wherein the outer peripheral wall comprises at least an outer surface and an inner surface opposite the outer surface, the inner surface defining an interior cavity disposed within the housing; a fan disposed within the interior cavity;

a plurality of slots in the outer peripheral wall, the plurality of slots disposed directly above the fan and operable to receive ambient air continually pulled from an environment outside of the housing into the interior cavity by the fan;

one or more buttons disposed on the outer surface of the outer peripheral wall, wherein each of the one or more buttons is operable to be independently selected to indicate that the monitoring device is in use by a unique user;

a sensor comprising:

a printed circuit board (PCB) disposed in a first plane that is vertically offset from a second plane, wherein the PCB continually receives the ambient air including the volatile organic compounds, and wherein the sensor detects a change in resistance associated with a presence of the volatile organic compounds;

a film disposed in the second plane; and a support plate, wherein the support plate is affixed to the film such that a space is formed between the film and the PCB;

a resistance gauge configured to measure the change in resistance of the sensor as a semiconductive material of the film is exposed to the ambient air; and a processor operatively coupled with the sensor and programmed with executable instructions that cause the processor to:

receive the detected change in resistance from the sensor as a measurement;

calculate the change in resistance over a period of time as ambient air is continually pulled into the interior cavity; and transmit, via a wireless transmitter operatively coupled with the processor, the calculated change in resistance over the period of time to a web server in electronic communication with the monitoring device over a network, wherein the web server compares the calculated change in resistance over the period of time to a baseline level of resistance associated with the unique user and determines a set of dietary recommendations associated with an intestinal microbiome of the unique user.

14. The monitoring device of claim 13, wherein the semiconductive material is configured to change the resistance of the sensor when exposed to the ambient air.

15. The monitoring device of claim 13, wherein the semiconductive material is configured to alter a resistance of gas molecules in the ambient air.

16. The monitoring device of claim 13, wherein the PCB comprises a communications terminal, the communications terminal configured to communicate with a downstream entity via an electronic network.

17. The monitoring device of claim 13, further comprising a user interface configured to receive biometric data of a unique user to determine that the monitoring device is in use by the unique user.

18. The monitoring device of claim 13, wherein the volatile organic compounds include short chain fatty acids.

19. The monitoring device of claim 13, wherein the sensor is configured to dissociate atmospheric gas molecules in the ambient air into charged ions.

20. The monitoring device of claim 19, wherein the resistance gauge is configured to measure the change of the resistance based on a dissociation of the atmospheric gas molecules.

* * * * *